US009085591B2

(12) United States Patent
Zhang et al.

(10) Patent No.: US 9,085,591 B2
(45) Date of Patent: Jul. 21, 2015

(54) ORGANOSILICON AMINE ELECTROLYTE MATERIALS CONTAINING POLYETHER CHAIN AND APPLICATION THEREOF IN ELECTROLYTES OF LITHIUM-ION BATTERIES

(75) Inventors: Lingzhi Zhang, Guangdong (CN); Hao Luo, Guangdong (CN); Xinyue Zhao, Guangdong (CN)

(73) Assignee: GUANGZHOU INSTITUTE OF ENERGY CONVERSION, CHINESE ACADEMY OF SCIENCES, Guangzhou, Guangdong (CN)

( * ) Notice: Subject to any disclaimer, the term of this patent is extended or adjusted under 35 U.S.C. 154(b) by 257 days.

(21) Appl. No.: 13/702,576

(22) PCT Filed: Mar. 10, 2011

(86) PCT No.: PCT/CN2011/071660
§ 371 (c)(1),
(2), (4) Date: Dec. 6, 2012

(87) PCT Pub. No.: WO2011/153854
PCT Pub. Date: Dec. 15, 2011

(65) Prior Publication Data
US 2013/0084490 A1    Apr. 4, 2013

(30) Foreign Application Priority Data
Jun. 7, 2010  (CN) .......................... 2010 1 0196365

(51) Int. Cl.
*C07F 7/18* (2006.01)
*C07F 7/10* (2006.01)
*H01M 10/056* (2010.01)
*C07F 7/08* (2006.01)
*H01M 10/0565* (2010.01)
*H01M 10/0525* (2010.01)
*H01M 10/0567* (2010.01)
*H01G 11/62* (2013.01)

(52) U.S. Cl.
CPC ............ *C07F 7/1852* (2013.01); *C07F 7/0818* (2013.01); *C07F 7/0854* (2013.01); *C07F 7/10* (2013.01); *C07F 7/184* (2013.01); *C07F 7/1836* (2013.01); *H01G 11/62* (2013.01); *H01M 10/056* (2013.01); *H01M 10/0525* (2013.01); *H01M 10/0565* (2013.01); *H01M 10/0567* (2013.01); *C07F 7/1844* (2013.01); *C07F 7/1848* (2013.01); *Y02E 60/122* (2013.01); *Y02E 60/13* (2013.01)

(58) Field of Classification Search
CPC ........ H01M 10/56; C07F 7/1852; C07F 7/10; C07F 7/1844; C07F 7/1848
USPC .......................... 429/188; 556/423
See application file for complete search history.

(56) References Cited

U.S. PATENT DOCUMENTS 6,521,707 B2 *   2/2003  Podszun et al. ............... 525/123
2005/0170254 A1  8/2005  West
2007/0048621 A1  3/2007  Kashida

FOREIGN PATENT DOCUMENTS

CN       1976110      6/2007
CN       102074736 A   5/2011

OTHER PUBLICATIONS

International Search Report mailed on Jun. 23, 2011, for international application No. PCT/CN2011/071660.
Rossi, "Silicon-containing liquid polymer electrolytes for application in lithium ion batteries", Polym Int2009; 58: 267-272, Mar. 2009.
Zhang, "Highly conductive trimethylsilyl oligo(ethylene oxide) electrolytes for energy storage applications", J. Mater. Chem., 2008, 18, 3713-3717, Jul. 9, 2008.
Amine, "Novel silane compounds as electrolyte solvents for Li-ion batteries", Electrochemistry Communications 8 (2006) 429-433, Feb. 3, 2006.
Rossi, "Synthesis and Characterization of Tetra- and Trisiloxane-Containing Oligo(ethylene glycol)s-Highly Conducting Electrolytes for Lithium Batteries", Chem. Mater.2006,18,1289-1295, Feb. 8, 2006.

* cited by examiner

*Primary Examiner* — Stewart Fraser
*Assistant Examiner* — Rachel Zhang
(74) *Attorney, Agent, or Firm* — Winston Hsu; Scott Margo

(57) ABSTRACT

The invention provides an organosilicon amine electrolyte material containing a polyether chain, which has a wide range of applications, as well as an application of the electrolyte material in a lithium ion battery. The chemical structure thereof is as shown in Formula 1, wherein R1 and R2 are selected from the same or different C1-C10 alkyls; A is a polyether chain segment having the structure of $(CH_2)_nO[(CH_2)_mO]_x(CH_2)_y$, where n and m are integers from 0 to 10, and x is an integer from 1 to 10; R3, R4 and R5 are selected from the same or the different C1-C10 alkyls or alkoxyl groups, or are equivalent to $ANR_1R_2$ or $-O-SiR_6R_7R_8$ in structure; wherein $R_6$, $R_7$ and $R_8$ are C1-C10 alkyls.

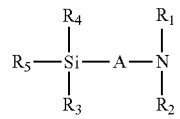

Formula 1

3 Claims, 4 Drawing Sheets

ORGANOSILICON AMINE ELECTROLYTE MATERIALS CONTAINING POLYETHER CHAIN AND APPLICATION THEREOF IN ELECTROLYTES OF LITHIUM-ION BATTERIES

BACKGROUND OF THE INVENTION

1. Field of the Invention

The invention relates to the technical field of chemical material synthesis and electrochemical energy storage, and in particular to synthesis of an organosilicon amine electrolyte material containing a polyether flexible molecular chain segment and an application thereof in an electrolyte of a lithium battery.

2. Description of the Prior Art

Currently, electrolyte materials used in the lithium ion battery industry are mainly systems of organic carbonate type compounds and $LiPF_6$ lithium salt, and the working mode of the system still has potential safety hazard in technology. The main reason is organic carbonate based electrolyte materials have very high flammability, and therefore there are huge hidden troubles in safety, and, especially in the application field of hybrid power and all-electric vehicles with the requirements of high safety, large capacity and high-rate discharge, the safety problem is an important factor restricting the applications of the materials. Therefore, active research and development are being conducted on a new generation of organic electrolyte materials which are safe, effective and environment-friendly both at home and abroad.

An organosilicon electrolyte material has the advantages of excellent thermal stability, low-temperature ionic conduction performance, high conductivity, nontoxicity, low flammability, high decomposition voltage and the like, and has higher electrochemical stability compared with carbon-based analogues. West et al. disclosed an organic silicon electrolyte material containing a polyalkoxylated ether in a patent (US publication number 20060035154 A1). Aurbach et al. reported that, by adding 1% of an organosilicon compound serving as an additive into a conventional electrolyte, high-temperature performances of a battery can be obviously improved (J. Electrochem. Soc., 147 (2000) 1322). However, research in this field still needs to be performed further so as to develop novel organic silicon electrolyte materials.

SUMMARY OF THE INVENTION

An object of the invention is providing an organosilicon amine electrolyte material containing a polyether chain, which has a wide range of applications, as well as an application of the electrolyte material in a lithium battery.

The chemical structure of the organosilicon amine electrolyte material containing the polyether chain of the invention is as shown in Formula 1.

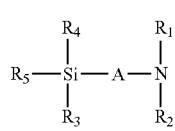

Formula 1 wherein, R1 and R2 are selected from the same or different C1-C10 alkyls; A is a polyether chain segment such as the structure of $(CH_2)_nO[(CH_2)_mO]_x(CH_2)_y$, where n and m are integers from 0 to 10, and x is an integer from 1 to 10; R3, R4 and R5 are selected from the same or the different C1-C10 alkyls or alcoxyl groups, or are equivalent to $ANR_1R_2$ or $—O—SiR_6R_7R_8$ in structure; and R6, R7 and R8 are the same or the different C1-C10 alkyls.

As to the organosilicon amine electrolyte material containing polyether chain of the invention, the polyether chain in the chemical structure of compound provides a complexation point with lithium ions for performing ion transport; and an amino group in the chemical structure can eliminate acidic substances generated by $LiPF_6$ hydrolysis of the existing carbonate based electrolyte system, thereby improving the performances of the battery.

The organosilicon amine electrolyte material containing the polyether chain of the invention can be used as an electrolyte or an additive to be applied to the lithium ion battery, and an electrolyte of the lithium ion battery comprises a lithium salt, a solvent with high dielectric constant or an organic solvent with low boiling point, and an organic silicon amine compound containing the polyether chain, which has the chemical structure as shown in the Formula 1.

The organosilicon amine electrolyte material containing the polyether chain of the invention can also be used as an electrolyte material to be applied to other electrochemical energy storage devices (such as electrolytic capacitors and super-capacitors) and other optoelectronic devices (such as organic solar cells and the like).

These and other objectives of the present invention will no doubt become obvious to those of ordinary skill in the art after reading the following detailed description of the preferred embodiment that is illustrated in the various figures and drawings.

DETAILED DESCRIPTION

Figure 1:
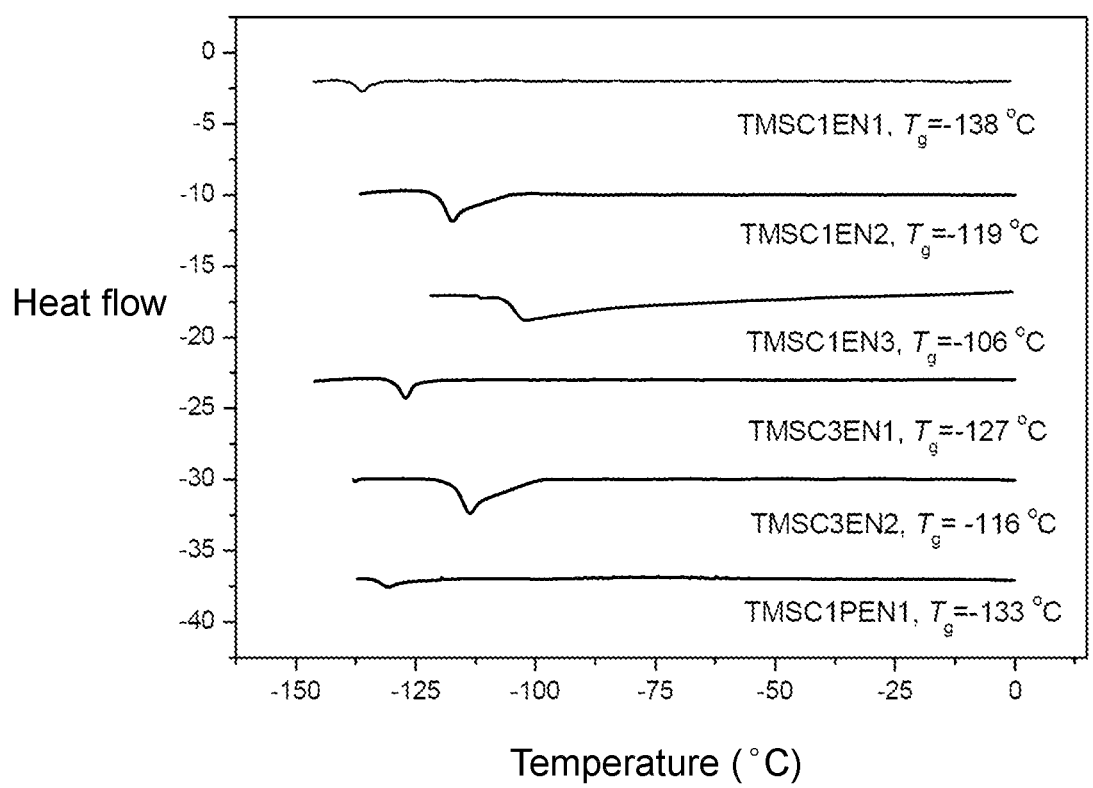
FIG. 1 shows the glass transition temperature curves of the compounds of embodiments 1-6 of the invention. A differential scan calorimeter is used for measuring glass transition temperatures of the compounds of the embodiments 1-6, and the glass transition temperatures of all the materials are relatively low.

The invention will be further described below in conjunction with the accompanying drawings and the embodiments.

According to an embodiment of the organic silicon amine electrolyte material containing a polyether chain, a preparation method comprises the following steps: transforming excess alkoxy alcohol amine compound and metal sodium to a corresponding alcohol sodium salt by reaction, then adding a chlorosilane compound at room temperature, increasing the temperature of a reaction system, and then reacting for 48 h; extracting a reaction crude product with n-hexane, and performing atmospheric distillation to get colorless liquid (reaction formula 1, and embodiments 1-5); and when n in the reaction formula 1 is 0, performing reflux reaction on the product of the embodiment through hexamethyldisilane amine and the corresponding alkoxy alcohol amine in the presence of a small amount of the metal sodium, and then performing direct distillation to get the product, and the embodiment 8 is one of such examples (n=0; m=2; x=1; y=2).

Reaction formula 1

HO[(CH$_2$)$_m$O]$_x$(CH$_2$)$_y$N(CH$_3$)$_2$

+ $\xrightarrow{Na}$ (R)$_3$Si(CH$_2$)$_n$Cl/[(CH$_3$)$_3$Si]$_2$NH (R)$_3$H$_3$Si—(CH$_2$)$_n$O[(CH$_2$)$_m$O]$_x$(CH$_2$)$_y$N(CH$_3$)$_2$

R = CH$_3$, CH$_3$CH$_2$O n = 0, 1, 3; m = 2-3; x = 0-3; y = 1, 2

The synthesis of the compound containing the longer polyether chain can be performed through the route in the embodiment 6 (as shown in reaction formula 2). The route comprises the following steps: first, transforming diol with the corresponding chain length, metal sodium and chlorosilane to an organic silicon alcohol compound by reaction; then transforming the organic silicon alcohol compound to a corresponding methyl sulfonic acid ester by reacting with methylsufonyl chloride, further transforming the methyl sulfonic acid ester to a corresponding organic silicon iodide by reacting with sodium iodide (NaI); and finally reacting with dimethylamine hydrochloride to get a corresponding organic silicon amine compound.

Reaction formula 2

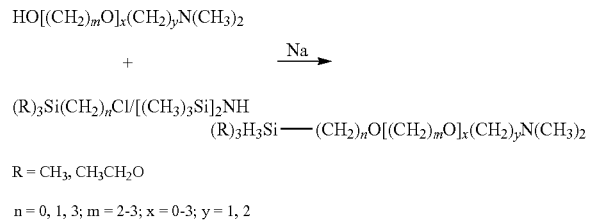

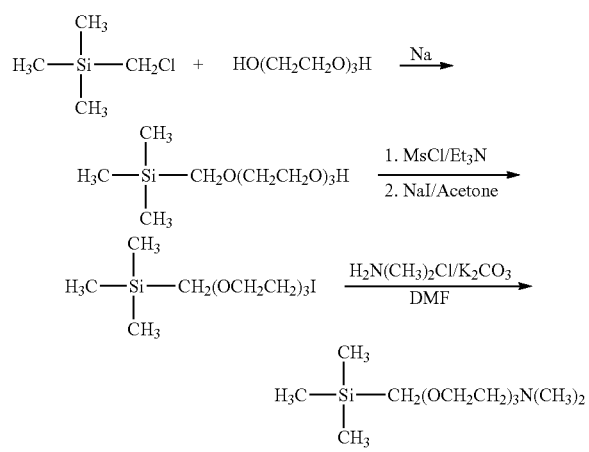

When more than one structure in R3, R4 and R5 structures is equivalent to ANR$_1$R$_2$ or the polyether chain structure, the synthesis of the embodiment can be performed as follows: enabling the corresponding chlorosilane and the corresponding alcohol amine and polyethylene glycol methyl ether to react in a tetrahydrofuran solvent, taking triethylamine as an acid scavenger and finally performing distillation to get the product. The embodiment 7 is one of such examples (n=1, reaction formula 3).

Reaction formula 3

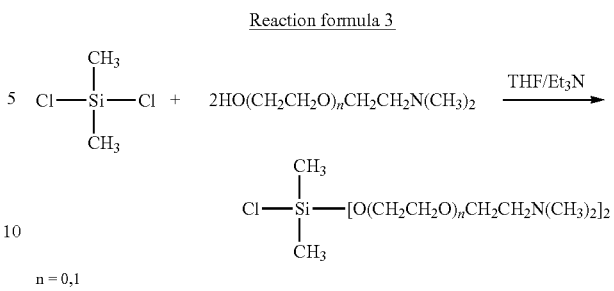

n = 0,1

When an organosilicon group is of siloxane, the synthesis of the compound is realized by performing addition reaction on olefins through Si—H bonds. The synthesis further comprises the following steps: firstly transforming the alkoxy alcohol amine compound and metal sodium to the corresponding alcohol sodium salt by reaction, then slowly adding allyl bromide at room temperature, reacting for a plurality of hours, then performing suction filtration, extraction, washing and drying, and distilling to get an allyl-substituted alkoxyamine compound; and then taking the equivalent allyl-substituted alkoxyamine compound and pentamethyl disiloxane under the protection of argon, increasing the temperature and reacting for several hours under the condition of being catalyzed by chloroplatinic acid, and finally distilling to get a disiloxane-substituted alkoxyamine compound (as in embodiments 9 and 10, reaction formula 4).

Reaction formula 4

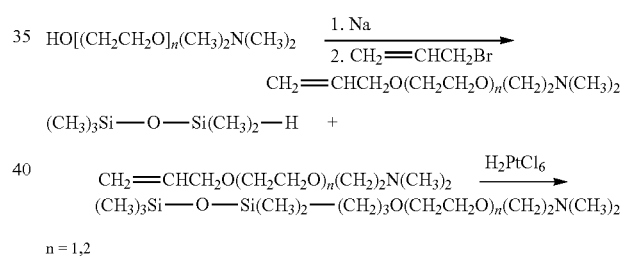

n = 1,2

The synthesis of the alkoxyamine compound containing alkoxy-substituted organic silicon can be performed through the route as shown in reaction formula 5. The route comprises the following steps: transforming the alkoxy alcohol amine compound and metal sodium to the corresponding alcohol sodium salt by reaction under the protection of argon, adding sodium iodide (catalytic amount) and chloropropyl triethoxysilane, reacting for a plurality of hours, then performing suction filtration, extraction, washing and drying, and distilling to get the target product (embodiment 11).

Reaction formula 5

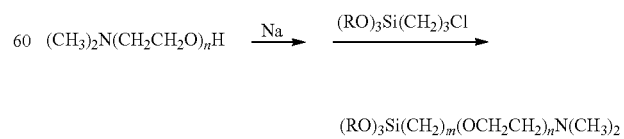

n = 1, 2

Embodiment 1

Synthesis of N,N-dimethyl-ethoxymethyl-trimethyl silane (TMSC1EN1)

The synthesis comprises the following steps: adding N,N-dimethyl ethanolamine (38 g, 0.42 mol) into a 250 mL two-neck round bottom flask, then adding metal sodium (3.6 g, 0.16 mol) into the reaction flask in a plurality of batches, heating to 80° C. till the sodium is completely reacted, then stopping heating, lowering the temperature to room temperature, adding chloromethyl trimethyl silane (20 g, 0.16 mol), stirring for half an hour at the room temperature, then starting to gradually increase the temperature to about 110° C., and reacting for 48 h; and extracting a reaction crude product with n-hexane, and performing atmospheric distillation to get a colorless liquid product. Yield: 66%, b.p.: 160° C.

$^1$H NMR (600 MHz, CDCl$_3$): −0.01 (s, 9H, SiCH$_3$), 2.22 (s, 6H, NCH$_3$), 2.38 (t, J=6.0, 2H, NCH$_2$), 3.07 (s, 2H, SiCH$_2$N), 3.45 (t, J=6.0, 2H, TMSC1OCH$_2$CH$_2$OCH$_2$).
$^{13}$C NMR (150.9 MHz, CDCl$_3$): 0.00, 49.17, 61.72, 68.30, 77.16.
$^{29}$Si NMR (119.3 MHz, CDCl$_3$): −2.62 ppm.

Embodiment 2

Synthesis of N,N-dimethyl-diethoxymethyl-trimethyl silane (TMSC1EN2)

N,N-dimethylamine ethoxyethanol is used as a reactant, the synthetic method which is the same as that in the embodiment 1 is adopted, and reduced-pressure distillation is performed on the product to get colorless liquid. Yield: 67%, b.p.: 34-35° C./0.2 mmHg.

$^1$H NMR (600 MHz, CDCl$_3$): δ=0.01 (s, 9H, SiCH$_3$), 2.24 (s, 6H, NCH$_3$), 2.47 (t, J=5.8, 2H, NCH$_2$), 3.12 (s, 2H, SiCH$_2$N), 3.55 (m, 6H, TMSC1OCH$_2$CH$_2$OCH$_2$).
$^{13}$C NMR (150.9 MHz, CDCl$_3$): −2.91, 46.02, 59.10, 65.53, 69.59, 70.35, 74.92.
$^{29}$Si NMR (119.3 MHz, CDCl$_3$): −2.99.

Embodiment 3

Synthesis of N,N-dimethyl-ethoxypropyl-trimethyl silane (TMSC3EN1)

3-chloropropyl trimethylsilane is used for replacing chloromethyl trimethyl silane as the reactant, the synthetic method which is the same as that in the embodiment 1 is adopted, and atmospheric distillation is performed on the product to get colorless liquid. Yield: 67%, b.p.: 201-203° C.

$^1$H NMR (600 MHz, CDCl$_3$): δ=−0.01 (s, 9H, SiCH$_3$), 0.47 (m, 2H, TMSCH$_2$), 1.60 (m, 2H, TMSCCH$_2$), 2.28 (s, 6H, NCH$_3$), 2.51 (t, J=5.7 Hz, 2H, CH$_2$NMe$_2$), 3.47 (tt, J=6.0, 7.2 Hz, 2H, SiCH$_2$N).
$^{13}$C NMR (150.9 MHz, CDCl$_3$): −0.00, 14.28, 25.77, 47.68, 60.75, 770.59, 75.99.
$^{29}$Si NMR (119.3 MHz, CDCl$_3$): 0.52 ppm.

Embodiment 4

Synthesis of N,N-dimethyl-diethoxypropyl-trimethyl silane (TMSC3EN2)

3-chloropropyl trimethylsilane is used for replacing the chloromethyl trimethyl silane as the reactant, the synthetic method which is the same as that in the embodiment 2 is adopted, and reduced-pressure distillation is performed on the product to get colorless liquid. Yield: 72%, b.p.: 53° C./0.2 mmHg.

$^1$H NMR (600 MHz, CDCl3): δ=−0.02 (s, 9H, SiCH$_3$), 0.47 (m, 2H, TMSCH$_2$), 1.58 (m, 2H, TMSCCH$_2$), 2.27 (s, 6H, NCH$_3$), 2.52 (t, J=6.0, 2H, CH$_2$NMe$_2$), 3.42 (t, J=7.2, 2H, SiCH$_2$N), 3.61 (m, 6H, TMSC$_3$OCH$_2$CH$_2$OCH$_2$).
$^{13}$C NMR (150.9 MHz, CDCl$_3$): 0.03, 14.24, 25.73, 47.70, 60.59, 71.18, 71.78, 72.18, 76.07.
$^{29}$Si NMR (119.3 MHz, CDCl$_3$): 0.491.

Embodiment 5

Synthesis of N,N-dimethyl-propoxy-trimethyl silane (TMSC1PrEN1)

N,N-dimethylamino propoxyethanol is used for replacing the N,N-dimethyl ethanolamine as the reactant, the synthetic method which is the same as that in the embodiment 1 is adopted, and atmospheric distillation is performed on the product to get colorless liquid. b.p.: 165° C./0.2 mmHg.

$^1$H NMR (600 MHz, CDCl$_3$): δ=0.04 (s, 9H, TMS), 1.72 (m, 2H, OCH$_2$), 2.22 (s, 6H, NMe$_2$), 2.31 (t, J=7.5 Hz, OCH$_2$CH$_2$), 3.08 (s, 2H, TMSCH$_2$), 3.42 (t, 2H, J=6.4 Hz, CH$_2$N).
$^{13}$C NMR (150.9 MHz, CDCl$_3$): 0.23, 31.14, 48.60, 59.79, 67.70, 76.49.
$^{29}$Si NMR (119.3 MHz, CDCl$_3$): −2.94.

Embodiment 6

Synthesis of N,N-dimethyl-triethoxymethyl-trimethyl silane (TMSC1EN3)

2-chloroethyl-diethoxymethyl-trimethyl silane is synthesized according to literature (*Heterocycles*, 41, (1995), 2665; *J. Chem. Soc., Chem. Commun.*, (6), (1991), 437). The synthesis comprises the following steps: dissolving dimethylamine hydrochloride (43.1 g, 0.528 mol) and anhydrous potassium carbonate (35.3 g, 0.256 mol) in 200 mL of dry N,N-dimethyl formamide (DMF), dissolving the chloroethyl-diethoxymethyl-trimethyl silane (20 g, 0.0585 mol) in 100 mL of DMF, and dripping into the reaction system at room temperature; continuing stirring for 2 h at the room temperature after the end of dripping, then increasing the temperature to 60° C. and reacting for 36 h; and pouring the reaction system into ice water, extracting with ether, performing rotary evaporation to remove ether, and performing reduced-pressure distillation to get a colorless liquid product. Yield: 76%, b.p.: 90° C./0.5 mmHg.

$^1$H NMR (600 MHz, CDCl3): δ=0.10 (s, 6H, Si(CH$_3$)$_2$), 2.22 (s, 12H, NCH$_3$), 2.45 (t, 4H, J=5.8 Hz, NCH$_2$CH$_2$), 3.523 (m, 8H, SiO(CH$_2$CH$_2$O)$_2$), 3.79 (t, 4H, J=5.4 Hz, NCH$_2$).
$^{13}$C NMR (150.9 MHz, CDCl$_3$): −0.00, 48.99, 61.98, 68.85, 72.56, 75.29.

Figure 2:
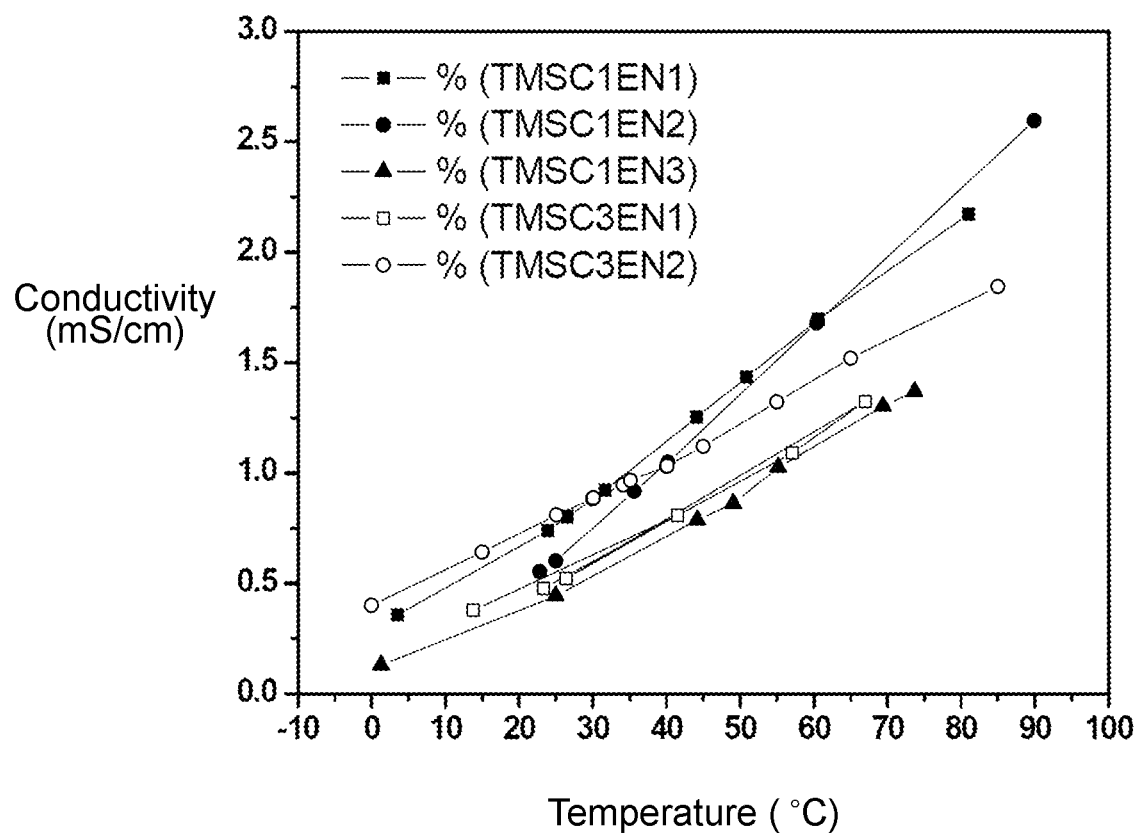
FIG. 2 shows the curves of ionic conductivity changing with the temperature (1M LiTFSI) of the compounds of the embodiments 1-5 of the invention. A lithium salt LiN$(CF_3S_2O_2)_2$ (LiTFSI) is dissolved in an electrolyte in the concentration of 1M prepared by the corresponding organosilicon amine compound containing an alkoxy group, and an ionic conductivity meter is used for measuring ionic conductivity under varied temperature of each compound.

A differential scan calorimeter is used for measuring glass transition temperatures of the compounds of the embodiments 1-6, and FIG. 1 shows that the glass transition temperatures of the materials are lower. In order to characterize the ionic conductivity of the material, a lithium salt LiN(CF$_3$S$_2$O$_2$)$_2$ is dissolved in the corresponding organic silicon amine compound to prepare an electrolyte in the concentration of 1M, an ionic conductivity meter is used for measuring the ionic conductivity under varied temperature and FIG. 2 shows curves of ionic conductivity changing with the temperature (1M LiTFSI) of the compounds of the embodiments 1-5 of the invention.

Embodiment 7

Synthesis of 2-(N,N-dimethyl-diethoxy)-dimethylsilane (DSEN2)

The synthesis comprises the following steps: slowly dripping dimethyldichlorosilane into tetrahydrofuran solution of N,N-dimethylamino ethoxyethanol (1.05 equivalent) and triethylamine (1.15 equivalent) under 0° C. ice-water bath, performing heating reflux for 16 h, performing reduced-pressure distillation to get a colorless liquid product. Yield: 98%, b.p.: 92° C./0.2 mmHg.

$^1$H NMR (600 MHz, CDCl$_3$): δ=0.10 (s, 6H, SiCH$_3$), 2.22 (s, 12H, NCH$_3$), 2.46 (t, 4H, J=5.8 Hz, NCH$_2$CH$_2$), 3.52 (m, 8H, SiOCH$_2$CH$_2$O), 3.79 (t, 4H, J=5.4 Hz, NCH$_2$).

$^{13}$C NMR (150.9 MHz, CDCl$_3$): −0.00, 48.99, 61.98, 64.85, 72.56, 75.29.

Embodiment 8

Synthesis of (N,N-dimethyl-diethoxy)-trimethyl silane (SEN2)

The synthesis comprises the following steps: mixing N,N-dimethylamino ethoxyethanol (24 g, 0.18 mol) with hexamethyldisilazane (29 g, 0.18 mol) at room temperature, further adding a small piece of metal sodium (0.16 g, 7.13 mmol), then performing heating reflux for 16 h, and directly performing reduced-pressure distillation on the product to get a colorless liquid product. Yield: 98%, b.p.: 90° C./0.5 mmHg.

$^1$H NMR (600 MHz, CDCl3): δ=0.07 (s, 9H, Si(CH$_3$)$_3$), 2.22 (s, 6H, N(CH$_3$)$_2$), 2.46 (t, 2H, J=6.0 Hz, NCH$_2$CH$_2$), 3.51 (m, 4H, SiOCH$_2$CH$_2$O), 3.68 (t, 2H, J=6.0 Hz, NCH$_2$CH$_2$).

$^{13}$C NMR (150.9 MHz, CDCl$_3$): 2.08, 48.47, 61.43, 64.49, 72.05, 74.92.

$^{29}$Si NMR (119.3 MHz, CDCl$_3$): 17.23.

Embodiment 9

Synthesis of N,N-dimethylamino-ethoxy propyl pentamethyl disiloxane (PMSC$_3$N$_1$)

The synthesis comprises the following steps: taking 0.33 mol of N,N-dimethylamino-ethanol (n=1) under the protection of argon, dissolving in 130 mL of dry THF, slowly adding 0.33 mol of metal sodium, heating to 80° C. till the sodium is completely reacted, placing in an ice bath for cooling, slowly adding 0.33 mol of allyl bromide after 0.5 h, reacting for 3 h at the temperature, then increasing the temperature to room temperature, stirring overnight, stopping reaction, then performing reduced-pressure suction filtration, washing with n-hexane, merging n-hexane phases, washing with a saturated sodium bicarbonate solution three times, drying with anhydrous magnesium sulfate, performing rotary evaporation, and then performing atmospheric distillation to get an allyl-substituted ethoxyamine compound; and taking 82.3 mmol of allyl-substituted ethoxyamine and 93.7 mmol of pentamethyl disiloxane (n=1) under the protection of argon, mixing and stirring for 0.5 h, then adding 0.4% mmol of H$_2$PtCl$_6$, gradually increasing the temperature to 90° C., reacting for a plurality of hours, and further performing reduced-pressure distillation to get a target product, namely colorless transparent liquid. b.p.: 47° C. (0.7 mmHg), yield: 85%.

N,N-dimethylamino ethyl allyl ether:

$^1$H NMR (600 MHz, CDCl$_3$): 5.88~5.93 (m, 1H, C=CH—C—O), 5.14~5.22 (m, 2H, CH$_2$=CH—C), 3.97 (m, 2H, C=C—CH$_2$—O), 3.49~3.51 (m, 2H, —C—O—CH$_2$—), 2.49 (t, 2H, —CH$_2$—N), 2.24 (s, 6H, —N(CH$_3$)$_2$).

$^{13}$C NMR (150.9 MHz, CDCl$_3$): 134.87, 117.01, 72.12, 68.09, 58.92, 45.85.

N,N-dimethylamino-ethoxy propyl pentamethyl disiloxane:

$^1$H NMR (600 MHz, CDCl$_3$): 3.49~3.52 (t, 2H, —O—CH$_2$—C—N), 3.36~3.40 (t, 2H, CH$_2$—O—C—C—N), 2.47~2.50 (t, 2H, —CH$_2$—N), 2.26 (s, 6H, —N(CH$_3$)$_2$), 1.57~1.61 (m, 2H, ~CH$_2$—C—Si), 0.46~0.50 (m, 2H, —C—CH$_2$—Si), 0.02~0.05 (d, 15H, —SiCH$_3$).

$^{13}$C NMR (150.9 MHz, CDCl$_3$): 74.08, 58.92, 45.85, 23.38, 14.26, 1.92, 0.22.

Embodiment 10

Synthesis of N,N-dimethylamino-diethoxy propyl pentamethyl disiloxane (PMSC$_3$N$_2$)

N,N-dimethylamino ethoxy ethanol (n=2) is used for replacing N,N-dimethylamino-ethanol as the reactant, the synthetic method which is the same with that in the embodiment 9 is adopted, and reduced-pressure distillation is performed on the product to get a product, namely colorless transparent liquid. b.p.: 98° C. (3.0 mmHg), yield: 74%.

N,N-dimethylamino diethyl allyl ether:

$^1$H NMR (600 MHz, CDCl$_3$): 5.80~5.85 (m, 1H, C=CH—C—O), 5.08~5.25 (m, 2H, CH$_2$=CH—C), 3.94 (m, 2H, C=C—CH$_2$—O), 3.49~3.55 (m, 6H, O—CH$_2$—CH$_2$—O—CH$_2$—), 2.43 (t, 2H, —CH$_2$—N), 2.18 (s, 6H, —N(CH$_3$)$_2$).

$^{13}$C NMR (300 MHz, CDCl$_3$): 134.56, 116.80, 72.00, 70.21, 69.24, 69.20, 58.62, 45.67.

N,N-dimethylamino-diethoxy propyl pentamethyl disiloxane:

$^1$H NMR (600 MHz, CDCl$_3$): 3.56~3.61 (m, 6H, —O—CH$_2$—CH$_2$—O—CH$_2$—C—N), 3.39~3.42 (t, 2H, O—CH$_2$—C—C—Si), 2.49~2.51 (t, 2H, —CH$_2$—N), 2.25 (s, 6H, —N(CH$_3$)$_2$), 1.57~1.60 (m, 2H, —CH$_2$—C—Si), 0.46~0.49 (m, 2H, —C—CH$_2$—Si), 0.02~0.04 (d, 15H, —Si—CH$_3$).

$^{13}$C NMR (150.9 MHz, CDCl$_3$): 74.22, 70.40, 70.02, 69.35, 58.82, 45.85, 23.38, 14.19, 1.93, 0.23.

Embodiment 11

Synthesis of N,N-dimethylamino-diethoxy propyl triethoxysilane (TEOSC3N2)

The synthesis comprises the following steps: taking 0.11 mol of metal sodium, adding into 0.11 mol of N,N-dimethylamino ethoxyethanol under the protection of argon, stirring, gradually increasing the temperature to 100° C. till the sodium is completely reacted, then stopping heating, lowering the temperature to 80° C., adding 50 ml of dry THF, reducing the temperature to 60° C., sequentially adding 20% mol of sodium iodide and 0.11 mol of 3-chloropropyl triethoxysilane, and stirring overnight at the temperature; cooling to room temperature, performing reduced-pressure suction filtration, washing with n-hexane, merging organic phases, then drying with anhydrous magnesium sulfate, further performing filtration at normal pressure, removing a solvent in filtrate by a rotary evaporator, performing reduced-pressure distillation to get a product, namely light yellow transparent liquid. b.p.: 97-98° C. (3 mm Hg), yield: 14.36%.

$^1$H NMR (600 MHz, CDCl$_3$): 3.77~3.78 (m, 6H, C—CH$_2$—O—Si—), 3.54~3.57 (m, 6H, O—CH$_2$—CH$_2$—O—CH$_2$—), 3.40 (m, 2H, Si—C—C—CH$_2$—O), 3.12 (s, 2H, O—CH$_2$—Si), 2.47 (m, 2H, —CH$_2$—N), 2.23 (s, 6H, —N(CH$_3$)$_2$), 1.66 (m, 2H, Si—C—CH$_2$), 1.17 (m, 9H, Si—C—CH$_3$), 0.59 (m, 2H, Si—CH$_2$—C).

$^{13}$C NMR (150.9 MHz, CDCl$_3$): 73.62, 70.39, 69.99, 69.35, 58.82, 58.35, 45.84, 22.92, 18.25, 6.42.

When the compound of the invention is applied to a lithium battery, manufacture can be performed according to the following steps.

A solvent with high dielectric constant is not particularly limited and is of the common solvent in the battery field generally, such as cyclic carbonates, like ethylene carbonate, propylene carbonate or γ-butyrolactone and the like. An organic solvent with low boiling point is also not particularly limited and can be of diethyl carbonate, dimethyl carbonate, ethyl methyl carbonate dimethoxyethane or fatty acid ester derivatives and the like. The volume ratio of the solvent with the high dielectric constant to the organic solvent with the low boiling point is 1:1 to 1:9, and the solvent with the high dielectric constant and the organic solvent with the low boiling point can also be used alone. A lithium salt can be of the lithium salt which is commonly used in the lithium battery. For example, the lithium salt optionally comprises at least one of the lithium salts including LiClO$_4$, LiCF$_3$SO$_3$, LiPF$_6$, LiN(CF$_3$SO$_2$)$_2$, LiBF$_4$, Li(BC$_4$O$_8$) and LiN(C$_2$F$_5$SO$_2$)$_2$. The concentration of the lithium salt in an organic electrolyte can be of 0.5-2.0M.

A positive pole active material, a conductive agent, a binding agent and a solvent are mixed for preparing a positive pole active material composition. The positive pole active material composition is directly coated on an Al collector body and dried for preparing a positive pole plate. Or, the positive pole active material composition is tape-casted on an independent substrate and laminated on the Al collector body from the obtained film of the positive pole active material composition for preparing the positive pole plate.

The positive pole active material can be any lithium-containing metal oxide which is commonly used in the art. Examples of the lithium-containing metal oxides comprise LiCoO$_2$, LiMn$_x$O$_{2x}$ (where x=1, 2), LiNi$_{1-x}$Mn$_x$O$_2$ (where 0<x<1), and LiNi$_{1-x-y}$Co$_x$Mn$_y$O$_2$ (where 0≤x≤0.5, 0≤y≤0.5) and LiFePO$_4$.

Carbon black can be used as the conductive agent. The binding agent can be selected from the group consisting of a vinylidene fluoride/hexafluoropropylene copolymer, polyvinylidene fluoride (PVDF), polyacrylonitrile, polymethylmethacrylate, polytetrafluoroethylene and mixtures thereof, or a styrene-butadiene rubber-based polymer. The solvent can be selected from the group consisting of N-methylpyrrolidone (NMP), acetone, water and the like. The amount of each of the positive pole active material, the conductive agent, the binding agent and the solvent can adopt the using amount which is commonly used in the lithium battery in the prior art.

Similarly, a negative pole active material, a conductive agent, a binding agent and a solvent are mixed for preparing a negative pole active material composition. The negative active material composition is directly coated on a Cu collector body, or tape-casted on the independent substrate and the negative active material film obtained therefrom is laminated on the Cu collector body to get a negative pole plate. The amount of each of the negative pole active material, the conductive agent, the binding agent and the solvent can be that commonly used in the lithium battery in the prior art.

Silicon metal, a silicon thin film, lithium metal, lithium alloy, a carbonaceous material or graphite can be used as the negative pole active material. The conductive agent, the binding agent and the solvent in the negative pole active material composition can be the same as those in the positive pole active material composition. If necessary, a plasticizer can be added into the positive pole active material composition and the negative pole active material composition to produce holes in the pole plates.

A separator can be made of any material which is commonly used in the lithium battery. Materials with low impedance against the movement of ions of the electrolyte and good capability of absorbing the electrolyte can be used. For example, the material can be nonwoven fabric or woven fabric selected from the groups consisting of glass fiber, polyester, Teflon, polyethylene, polypropylene, polytetrafluoroethylene (PTFE), and combinations thereof. More specifically, the lithium ion battery can use a windable separator which comprises one of polyethylene, polypropylene and the like, and the lithium ion battery can use the separator with excellent capacity of impregnating the organic electrolyte.

As described above, in the lithium battery adopting the electrolyte prepared by mixing the alkoxy-containing organic silicon amine electrolyte material according to an appropriate proportion, a uniform and stable protection layer can be formed, and the efficiency of the battery can be improved in comparison with the prior art.

The invention will be further described through the following embodiment, but the invention is not limited thereto.

Embodiment 12

Manufacturing and Testing of Battery

In the experiment conducted, as for the electrolyte being used, LiPF$_6$ is purchased from Zhangjiagang Guotai-Huarong New Chemical Materials Co., Ltd., LiFePO$_4$ is from Tianjin Stellan Energy Technology Co., Ltd., and the separator is a product of Asahi Chemical Industry Co., Ltd. The preparation of the electrolyte and the assembly of the battery are performed under an argon atmosphere (the purity is larger than 99.9999%).

LiPF$_6$ is dissolved in ethylene carbonate and diethyl carbonate (EC:DEC=1:2) to prepare the electrolyte in the concentration of 1M, and 3 wt % of the TMSC1EN2 is added into the electrolyte. LiFePO$_4$ and metal lithium are respectively used as a positive pole and a negative pole to assembly a coin type battery (2025), and then charge/discharge testing is performed in a battery charge-discharge testing system from Shenzhen Sunway, with a charge-discharge voltage of 2.5V-4.1V. The battery of the embodiment 6 is charged by 0.1 C or 0.2 C constant current, and then constant-current discharge is performed, with a discharge rate of 0.1 C or 0.2 C.

Figure 3:
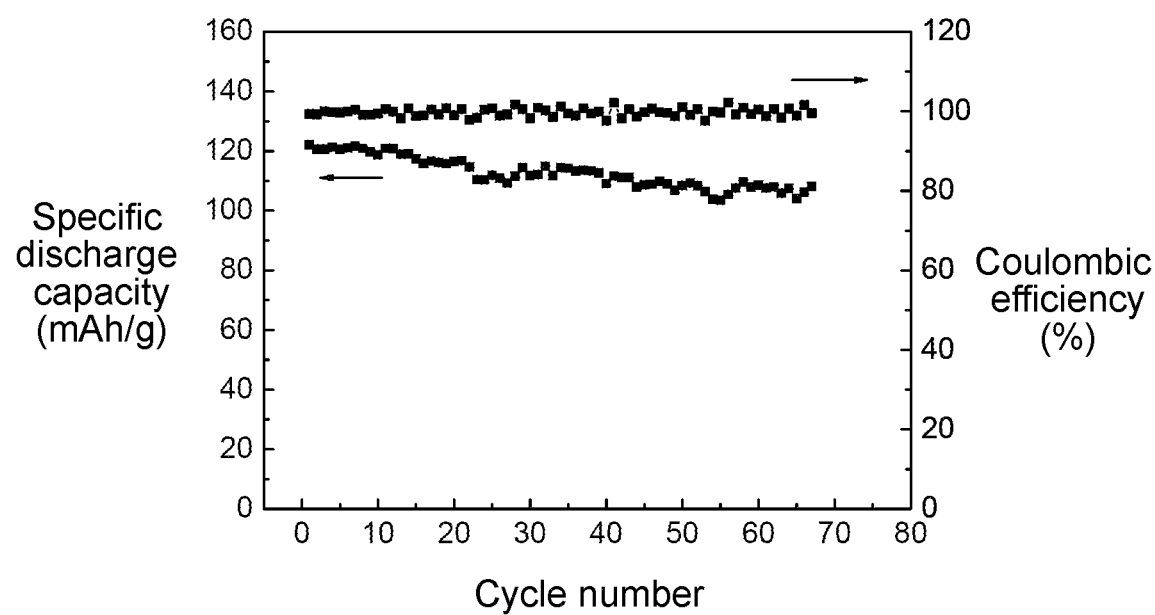
FIG. 3 is a 0.2 C charge and discharge cycle performance and battery efficiency curve of a battery comprising the compound of the embodiment 2 of the invention.

FIG. 3 is a 0.2 C charge and discharge cycle performance and battery efficiency curve of an electrolyte battery of the compound of the embodiment 2 of the invention, and the battery shows 100% efficiency and stable cyclic charge-discharge performance.

Contrast Example 1

Figure 4:
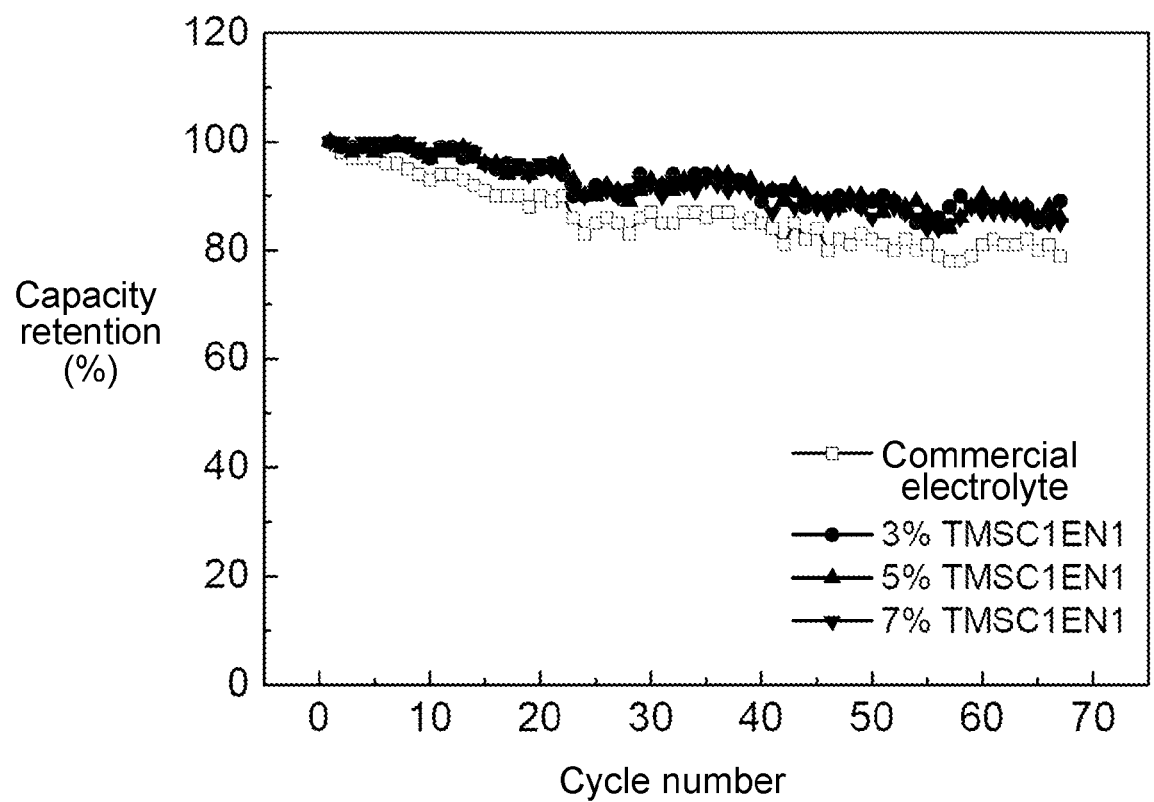
FIG. 4 shows the capacity retention rate curves of a commercial electrolyte (1M LiPF6 EC/DEC=1/2+1% VC+1% VEC) reference battery of a contrast example 1 and the batteries to which a N2 compound is added in different proportions (3%, 5% and 7%) under the same test conditions.

In order to make a contrast, the coin type battery (2025) is assembled by using a commercial electrolyte (1M $LiPF_6$, EC:DEC=1:2, 1% of vinylene carbonate VC and 1% of vinyl ethyl carbonate VEC) according to the same method as in the embodiment 12; then the charge/discharge comparison testing is performed by the same method as in the embodiment 9 under the rate of 0.2 C, and the battery in the contrast example could not be charged to 4.1V under the rate of 0.1 C. Under the same testing conditions, the capacity of the battery to which part of N2 compound (3%, 5% and 7%) is added is substantially equivalent to that of the battery in the contrast example (as shown in FIG. 4), the first capacity being 122 mAh/g; and the cycle performance of the battery to which the N2 compound is added is improved in comparison with the commercial electrolyte battery, with the capacity retention rate above 85%, while the capacity retention rate of the commercial electrolyte battery is only 79%, and therefore adding a small amount of the N2 compound in the commercial electrolyte could effectively improve the cycle performance of the battery.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An organosilicon amine electrolyte material containing a polyether chain, having a chemical structure as shown in Formula 1:

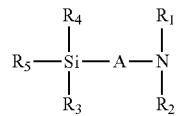

Formula 1 wherein $R_1$ and $R_2$ are selected from the same or different C1-C10 alkyl groups; A is a polyether chain segment having the structure of $(CH_2)_nO[(CH_2)_mO]_x(CH_2)_y$, where n and m are integers from 1 to 10, and x is an integer from 1 to 10, y is 1 or 2; $R_3$, $R_4$ and $R_5$ are selected from the same or the different C1-C10 alkyl or alkoxyl groups, or are equivalent to $ANR_1R_2$ or —O—$SiR_6R_7R_8$ in structure; wherein $R_6$, $R_7$ and $R_8$ are the same or the different C1-C10 alkyl groups.

2. An application of the organosilicon amine electrolyte material containing the polyether chain as in claim 1 in an electrolyte of a lithium-ion battery.

3. The application of the organosilicon amine electrolyte material containing the polyether chain in the electrolyte of the lithium-ion battery as in claim 2, wherein the organosilicon amine electrolyte material containing the polyether chain, serving as an electrolyte material or an additive, is applied to the lithium ion battery, the electrolyte of the lithium ion battery comprising a lithium salt, a solvent with high dielectric constant or an organic solvent with low boiling point, and an organic silicon amine compound containing the polyether chain, which has the chemical structure as shown in the Formula 1.

* * * * *